United States Patent [19]

Patel

[11] Patent Number: 4,820,691
[45] Date of Patent: Apr. 11, 1989

[54] AMINO ACID 1,2-DIKETO DERIVATIVES AS RENIN INHIBITORS

[75] Inventor: Dinesh V. Patel, Somerset, N.J.

[73] Assignee: E. R. Squibb & Sons, Inc., Princeton, N.J.

[21] Appl. No.: 66,596

[22] Filed: Jun. 24, 1987

[51] Int. Cl.⁴ .................. A61K 37/43; C07K 5/06; C07K 5/08; C07D 279/10; C07D 265/30; C07D 241/04; C07D 211/60; C07D 211/70

[52] U.S. Cl. .................. 514/19; 530/331; 530/332; 514/18; 540/544; 540/575; 540/607; 544/58.4; 544/168; 544/390; 546/245; 546/336; 548/200; 548/215; 548/341; 548/494; 548/538; 548/540; 564/157; 564/159

[58] Field of Search .................. 514/19, 18; 530/331, 530/332; 540/544, 575, 607; 544/58.4, 168, 390; 546/245, 336; 548/200, 215, 341, 494

[56] References Cited

FOREIGN PATENT DOCUMENTS 5288186 1/1986 Australia .
0104041 3/1984 European Pat. Off. .
0190891 1/1985 European Pat. Off, .
201036 9/1984 Japan .

OTHER PUBLICATIONS

Chem. Abstr., vol. 106, 85059.
Powers et al., "Inhibition of Human Leukocyte Elastase, Porcine Pancreatic Elastase and Cathepsin G by Pepside Ketones", Proceedings from the 9th American Peptide Symposium, Jun. 23-28, 1985, Univ. of Toronto, Canada.
Chem. Abstr., vol. 104, 22120u.
Chem. Abstr., vol. 89, 19797o.

*Primary Examiner*—Delbert R. Phillips
*Attorney, Agent, or Firm*—Theodore R. Furman, Jr.

[57] ABSTRACT

Compounds of the formula

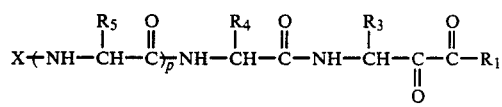

are disclosed. These compounds interevene in the conversion of angiotensin to angiotensin II by inhibiting renin and thus are useful as anti-hypertensive agents.

11 Claims, No Drawings

AMINO ACID 1,2-DIKETO DERIVATIVES AS RENIN INHIBITORS

FIELD OF THE INVENTION

The present invention relates to amino acid derivatives and more particularly concerns 1,2-diketo derivatives useful, for example, as renin inhibitors.

BACKGROUND OF THE INVENTION

Szelke et al., in European Patent Application No. 0,104,041 A1, disclose various polypeptide analogues. These analogues, useful as renin inhibitors, include polypeptide 1,2-ketoamides wherein the amide group comprises a peptidic function.

In Australian Patent Abstract No. AU-A-52881/86, Kolb et al. disclose new activated electrophilic ketone-bearing peptidase inhibitors. Among the analogues disclosed are polypeptidyl 1,2-hydroxy esters and 1,2-keto esters useful for renin inhibition.

Kubota et al., in European Patent Application No. 0,190,891 A2, disclose amino acid derivatives of the formula

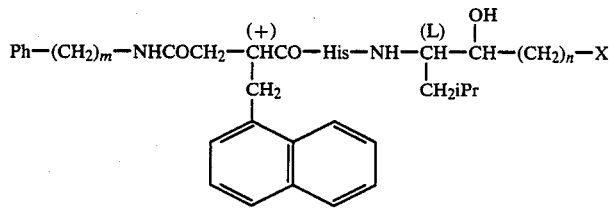

wherein when n=0, polypeptidyl 1,2-hydroxy esters are provided. These compounds are also disclosed as having activity as renin inhibitors.

Matsueda et al., in Japanese Patent No. J6 1078-795-A, disclose peptides of the formula

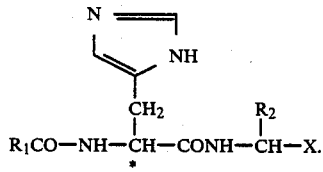

When X is

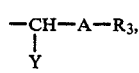

Y is hydroxy, A is a single bond, and $R_3$ is optionally protected carboxy, acyl; 1,2-hydroxy esters and 1,2-hydroxy ketones, useful as renin inhibitors, are provided.

SUMMARY OF THE INVENTION

In accordance with the present invention new diketone derivatives useful as renin inhibitors are disclosed. These compounds have the formula

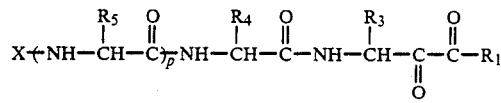

wherein
X is $R_6$—$(CH_2)_m$—,

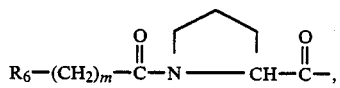

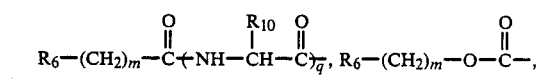

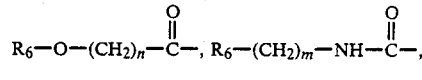

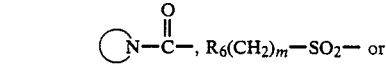, $R_6(CH_2)_m$—$SO_2$— or

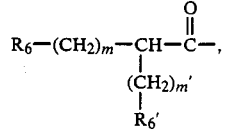

$R_1$ is hydrogen, alkyl, arylalkyl, aryl, heteroalkyl or a fully saturated, partially saturated, or unsaturated monocyclic heterocyclic ring of 5 or 6 atoms. The heterocyclic ring is attached to

by way of an available carbon atom.

represents a heterocyclic ring of the formula

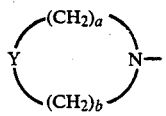

wherein Y is —CH$_2$, O, S, or N—R$_9$, a is an integer from 1 to 4, and b is an integer from 1 to 4 provided that the sum of a plus b is an integer from 2 to 5;

R$_3$, R$_4$, R$_5$ and R$_{10}$ are independently selected from hydrogen, lower alkyl, halo substituted lower alkyl, —(CH$_2$)$_n$-aryl, —(CH$_2$)$_n$-heterocyclo, —(CH$_2$)$_n$—OH, —(CH$_2$)$_n$—O-lower alkyl, —(CH$_2$)$_n$—NH$_2$, —(CH$_2$)$_n$—SH, —(CH$_2$)$_n$—S-lower alkyl, —(CH$_2$)$_n$—O—(CH$_2$)$_g$—OH, —(CH$_2$)$_n$—O—(CH$_2$)$_g$—NH$_2$,

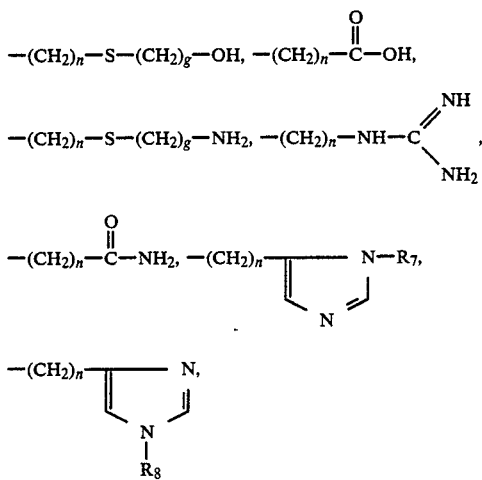

and —(CH$_2$)$_n$-cycloalkyl;

R$_6$ and R$_6'$ are independently selected from lower alkyl, cycloalkyl, aryl and heterocyclo;

p is zero or one;

q is zero or one;

m and m' are independently selected from zero and an integer from 1 to 5;

n is an integer from 1 to 5;

g is an integer from 2 to 5;

R$_7$ is

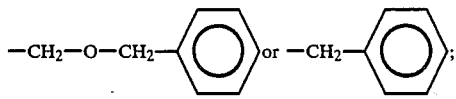

R$_8$ is 2,4-dinitrophenyl,

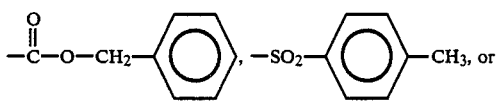

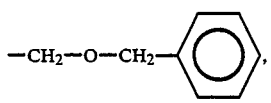

R$_9$ is hydrogen, lower alkyl,

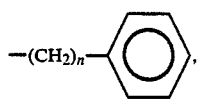

or —(CH$_2$)$_n$-cycloalkyl.

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons. Similarly, the terms lower alkoxy and lower alkylthio refer to such lower alkyl groups attached to an oxygen or sulfur. The preferred lower alkyl groups are straight or branched chain of 1 to 5 carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkythio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred hetero groups include 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

The compounds of formula I wherein X is

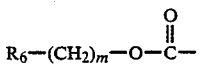

can be prepared by treating a compound of the formula

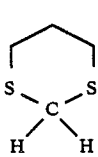

II with n-butyl lithium and thereafter reacting same with the starting material of the formula R$_1$-Halogen      III to provide a compound having the formula

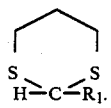

An N-protected amino acid ester of the formula

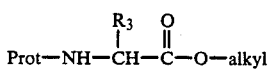

(wherein Prot is an amino protecting group such as t-butoxycarbonyl) is treated with lithium borohydride to give the alcohol of the formula

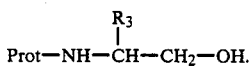

Treatment of the alcohol of formula VI with pyridine-sulfur trioxide complex or with periodinane reagent (see Dess et al., *J. Org. Chem.*, Vol. 48, p. 5155–5156 (1983)) produces an aldehyde of the formula

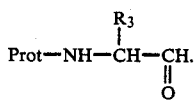

The aldehyde of formula VII is thereafter reacted with the compound of formula IV in the presence of n-butyl lithium to provide a compound of the formula

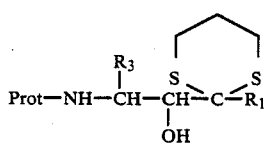

which can be deprotected such as by treatment with hydrochloric acid to provide the alcohol of the formula

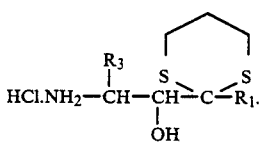

The alcohol of formula IX is thereafter coupled with a peptide of the formula

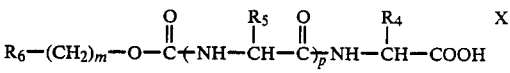

preferably in a solvent such as tetrahydrofuran or dimethylformamide and in the presence of hydroxybenzotriazole, a base such as N-methylmorpholine or diisopropylethyl amine, and a coupling agent such as dicyclohexylcarbodiimide to provide

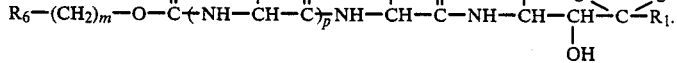

Compound XI is treated with an oxidizing agent, such as ammonium ceric nitrate or thallic nitrate to provide the hydroxy keto compound of the formula

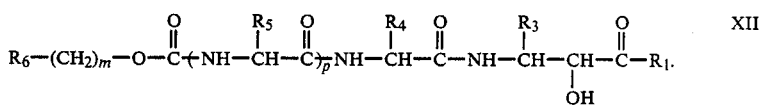

Treatment of the compound of formula XII with, for example, the periodinane reagent (cited above in the formation of compound VII) provides

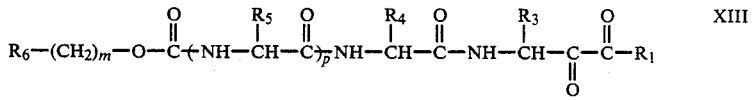

that is, compounds of formula I wherein X is

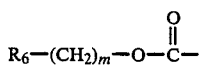

and p is one.

To prepare the compounds of the invention wherein X is

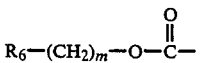

and p is zero, the amino alcohol of formula IX can be reacted with the amino acid of the formula

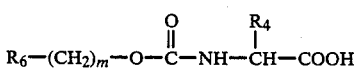

to yield the compounds of the formula

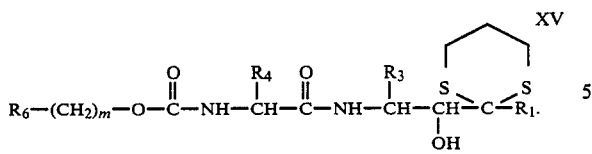

XV

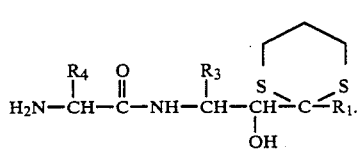

XIX

Compound XV is thereafter treated as compounds XI and XII above to provide the diketone derivatives wherein p is zero.

The compound of formula I wherein X is other than

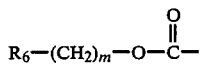

can be prepared by using compounds of formula XI wherein

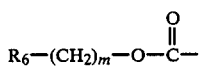

is either t-butoxycarbonyl or benzyloxycarbonyl as the starting material. Removal of the t-butoxycarbonyl or benzyloxycarbonyl by standard amine deprotecting means provides the intermediates of the formula

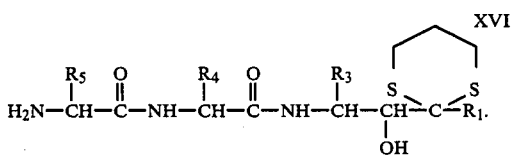

XVI

The amine of formula XVI is treated with the halide of the formula

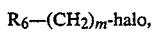 XVII particularly where halo is bromine, to provide the product

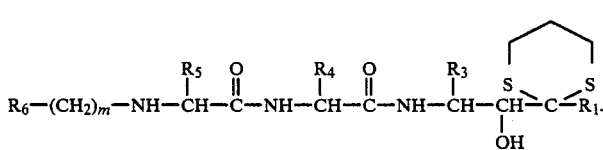

XVIII

Compound XVIII is thereafter treated as compounds XI and XII above to provide the diketone derivative of formula I wherein p is one and X is $R_6—(CH_2)_m—$.

Similarly, by starting with compound XV where

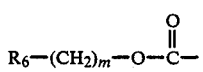

is either t-butoxycarbonyl or benzyloxycarbonyl, and carrying out standard amine deprotection, intermediates XIX can be obtained, The amine of formula XIX can thereafter be reacted with the halide of formula XVII to provide a compound of the formula

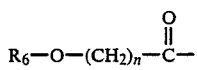

XX

Compound XX is thereafter treated as compounds XI and XII above to provide the products of formula I wherein X is $R_6—(CH_2)_m—$ and p is zero.

The compounds of formula I wherein X is

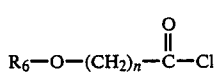

can be prepared by treating the amine of formula XVI or XIX with the acid chloride of the formula

 XXI in the presence of a base such as triethylamine, followed by treatment as with compounds XI and XII above.

The compounds of formula I wherein X is $R_6—(CH_2)_m—SO_2—$ can be prepared by treating the amine of formula XVI or XIX with the substituted sulfonyl chloride of the formula $R_6—(CH_2)_m—SO_2—Cl,$ XXII followed by treatment as with compounds XI and XII above.

The compounds of formula I wherein X is

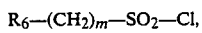

can be prepared by treating the amine of formula XVI or XIX with the acid chloride of the formula

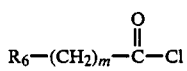 XXIII in the presence of triethylamine, followed by treatment as with XI and XII. Alternatively, these compounds can be prepared by coupling the carboxylic acid of the formula

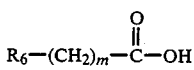   XXIV to the amine of formula XVI or XIX in the presence of a coupling agent, such as dicyclohexylcarbodiimide, and 1-hydroxybenzotriazole hydrate, followed by treatment as with compounds XI and XII.

The compounds of formula I wherein X is

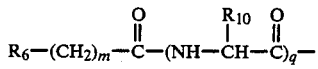

and q is one can be prepared by acylating the amino acid of the formula

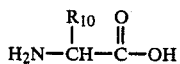   XXV with the acid chloride of formula XXIII in the presence of a base, such as sodium hydroxide, and in a solvent, such as tetrahydrofuran, and water to give the acylated amino acid of the formula

   XXVI

The amino acid of formula XXVI is then coupled to the amine of formula XVI or XIX in the presence of dicyclohexylcarbodiimide and 1-hydroxybenzotriazole hydrate followed by treatment as with compounds XI and XII to give the desired compounds of formula I.

The compounds of formula I wherein X is

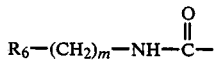

and p is one can be prepared by coupling an amino acid of the formula

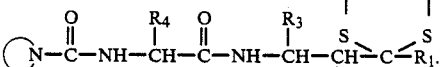   XXVII to the amine of formula XIX in the presence of a coupling agent, such as dicyclohexylcarbodiimide, and 1-hydroxybenzotriazole hydrate, followed by treatment as with compounds XI and XII.

Similarly, the compounds of formula I wherein X is

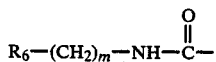

and p is zero can be prepared by coupling an amino acid of the formula

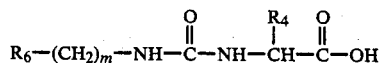   XXVIII to an amino alcohol of formula IX in the presence of a coupling agent, such as dicyclohexylcarbodiimide, and 1-hydroxybenzotriazole hydrate to provide a compound of the formula

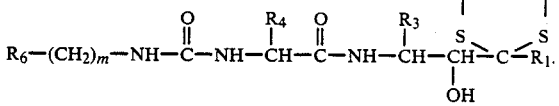   XXIX

Compound XXIX can thereafter be treated as compounds XI and XII above to provide the diketo compound of formula I wherein X is

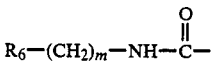

and p is zero.

The compounds of formula I wherein X is

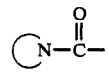

and p is one can be prepared by coupling an amino acid of the formula

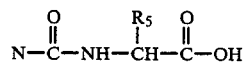   XXX to the amine of formula XIX in the presence of a coupling agent and 1-hydroxybenzotriazole hydrate, followed by treatment as with compounds XI and XII. Similarly the compound of formula I wherein X is

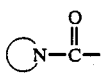

and p is zero can be prepared by coupling an amino acid of the formula

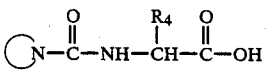   XXXI to the amino alcohol of formula IX in the presence of the above-described coupling agent and hydrate to provide a compound of the formula

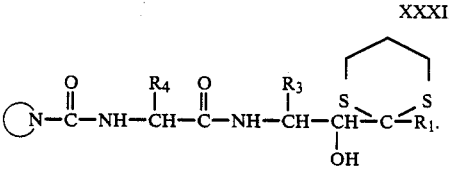   XXXII

Compound XXXII is thereafter treated as compounds XI and XII above to provide the diketone compounds of formula I wherein X is

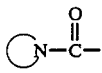

and p is zero.

The amino acid intermediates of formulas XXVII, XXVIII and XXXI can be prepared by treating an amine $R_6-(CH_2)_m-NH_2$ or

with phosgene and N-methylmorpholine followed by reaction with an amino acid methyl ester hydrochloride salt of the formula

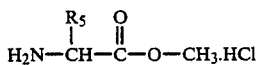
XXXIII or of the formula

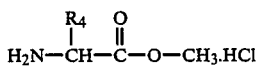
XXXIV in the presence of N-methylmorpholine. Removal of the methyl ester group by treatment with aqueous sodium hydroxide gives the desired intermediate.

The products of formula I wherein X is

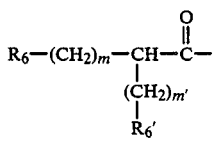

can be prepared by coupling the carboxylic acid of the formula

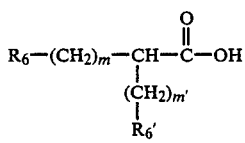
XXXV to the amine of formula XVI or XIX in the presence of dicyclohexylcarbodiimide and 1-hydroxybenzotriazole hydrate, followed by treatment as with compounds XI and XII. Alternatively, the acid of formula XXXV can be converted to the acid chloride and this acid chloride can then be coupled to the amine of formula XVI or XIX in the presence of triethylamine and tetrahydrofuran and followed by treatment as with compounds XI and XII.

The compounds of formula I wherein X is

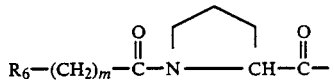

can be prepared by acylating proline with the acid chloride of formula XXIII in the presence of base such as sodium hydroxide, i.e., a pH of about 8, and a solvent mixture of tetrahydrofuran and water to give

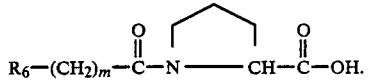
XXXVI

The acylated amino acid of formula XXXVI is then coupled to the amine of formula XVI or XIX in the presence of a coupling agent such as dicyclohexylcarbodiimide and 1-hydroxybenzotriazole hydrate, followed by treatment as with XI and XII.

In the above reactions, if any of $R_3$, $R_4$, $R_5$ and $R_{10}$ are $-(CH_2)_n$-aryl wherein aryl is phenyl, 1-naphthyl, 2-naphthyl substituted with one or more hydroxy or amino groups, $-(CH_2)_n$-heterocyclo wherein heterocyclo is an imidazolyl, $-(CH_2)_n-NH_2$, $-(CH_2)_n-SH$, $-(CH_2)_n-OH$,

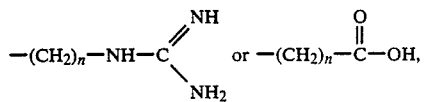

then the hydroxyl, amino, imidazolyl, mercaptan, carboxyl, or guanidinyl function should be protected during the reaction. Suitable protecting groups include benzyloxycarbonyl, t-butoxycarbonyl, benzyl, benzhydryl, trityl, tosyl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, the Peptides, Volume 1, "Major Methods of Peptide Bond Formation", Academic Press (1979).

Preferred compounds of this invention are those of formula I wherein
X is

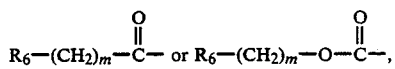

$R_6$ is selected from straight or branched chain lower alkyl of up to 5 carbons, cycloalkyl of 4 to 6 carbons, phenyl, 1-naphthyl, and 2-naphthyl;

m is selected from zero, one and two;

$R_1$ is alkyl, arylalkyl, aryl, or heteroaryl;

$R_3$ is straight or branched chain lower alkyl of 3 to 5 carbons, $-(CH_2)_n$-cyclopentyl, $-(CH_2)_n$-cyclohexyl, or

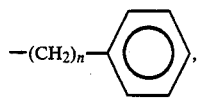

wherein n is an integer from 1 to 3;
R₄ is hydrogen, straight or branched chain lower alkyl of up to 5 carbons, —(CH₂)₄—NH₂,

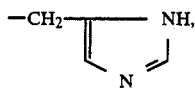

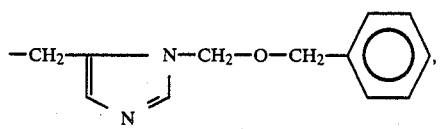

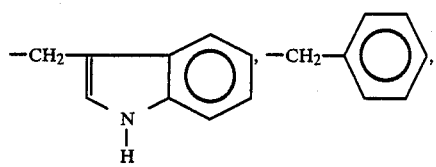

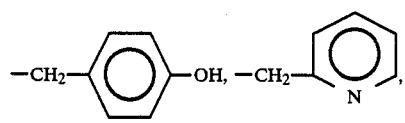

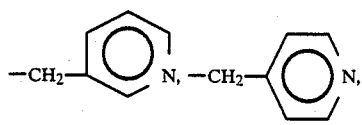

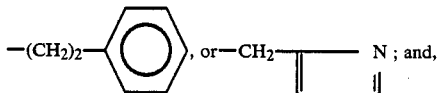

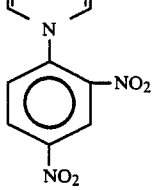

R₅ is straight or branched chain lower alkyl of up to 5 carbons,

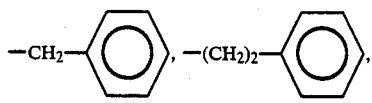

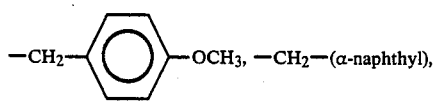

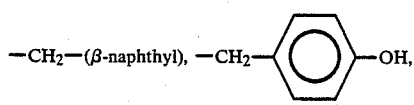

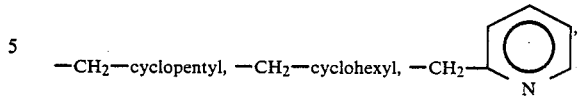

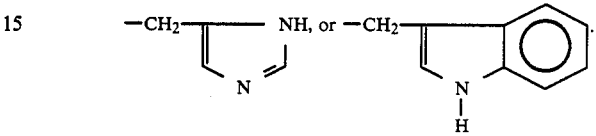

Most preferred are those compounds of formula I wherein

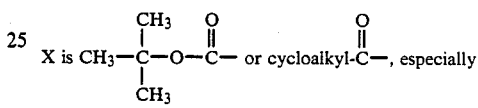

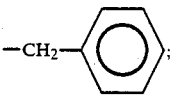

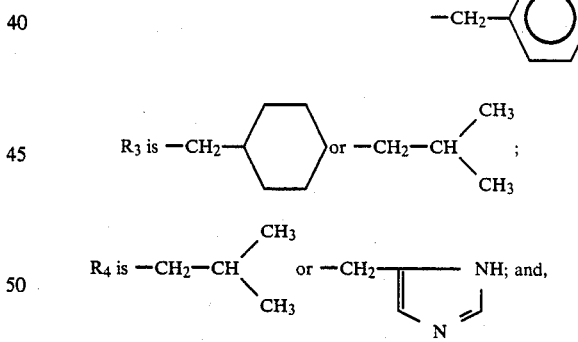

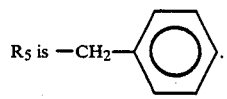

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of $R_3$, $R_4$, $R_5$ and $R_{10}$ are other than hydrogen and at the carbon to which the —OH group is attached. Thus, the compounds of formula I can exist in diastereoisomeric forms or in mixtures thereof. The above-described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg, preferably about 250 to 500 mg per kg of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg, preferably about 3000 to 4000 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations in such that a suitable dosage in the range indicated is obtained.

The present invention will now be described by the following examples, however, the invention should not be limited to the details therein.

EXAMPLE 1

(S)-[(1,1-Dimethylethoxy)carbonyl]-L-phenylalanyl-N-[1-(cyclohexylmethyl)-2,3-dioxohexyl]-L-leucinamide A. 2-Propyl-1,3-dithiane n-Butyl lithium (2.5M, 56.32 ml, 141 mmol) was added dropwise to a 500 ml tetrahydrofuran solution of 1,3-dithiane (15.42 g, 128 mmol) at −20°. After stirring for 2.5 hours at −20°, the solution was cooled to −78° and 1-iodopropane (12.5 ml, 128 mmol) was added to it in one portion. The reaction mixture was left for gradual warming (−78° to 0° C.) and overnight stirring (19 hours). Tetrahydrofuran was removed on the rotary evaporator, residue taken in ether (250 ml) and washed with water (200 ml). The aqueous layer was reextracted with ether (250 ml). Combined ethereal extracts were washed sequentially once with water, once with saturated sodium chloride, dried over anhydrous sodium sulfate and concentrated to give a yellow oil which on distillation under vacuum yielded 19.310 g of the title A compound.

B. [(1S)-1-(Cyclohexylmethyl)-2-hydroxy-2-(2-propyl-1,3-dithian-2-yl)ethyl]carbamic acid, 1,1-dimethylethyl ester n-Butyl lithium (2.5M, 11.76 ml, 29.4 mmol) was added dropwise at −25° to a 40 ml tetrahydrofuran solution of 2-n-propyl-1,3-dithiane from part A (4.536 g, 28.0 mmol). After stirring for 2 hours at −20° to −25°, the solution was cooled to −78° and (S)-<α-[[(1,1-dimethylethoxy)carbonyl]amino]cyclohexanepropanal (3.57 g, 14.0 mmol) was added as a 20 ml tetrahydrofuran solution. A chromatography check after 1 hour revealed the formation of a complex reaction mixture. It was warmed gradually from −78° to −50° over a period of 18 hours, quenched with saturated ammonium chloride (50 ml) and the two layers separated upon warming to room temperature. The aqueous layer was diluted with water (75 ml, to dissolve the precipitated ammonium chloride) and reextracted with ethyl acetate (2×50 ml). Combined organic extracts were washed with saturated ammonium chloride (1×75 ml), dried over anhydrous sodium sulfate and concentrated to give 7.9 g crude product which upon flash chromatographic purification yielded 1.517 g of the title B compound.

C. α-[(S)-1-Amino-2-cyclohexylethyl]-2-propyl-1,3-dithiane-2-methanol, monohydrochloride The title B compound (533 mg, 1.278 mmol) was dissolved in ethyl acetate (20 ml), cooled to 0° and the solution saturated by hydrogen chloride by bubbling the gas through it for a period of ∼5 minutes. A chromatography check revealed total disappearance of starting material. Ethyl acetate was removed on the rotary evaporator and the resulting yellow solid triturated with ether and filtered to give the title compound (370 mg) which looked pure by $^{13}C$ NMR.

D. t-Butyloxycarbonylphenylalanyl leucine, methyl ester

To a mixture of t-butyloxycarbonyl-L-phenylalanine (13.265 g, 50 mmol), L-leucine methyl ester (9.085 g, 50 mmol) and hydroxybenzotriazole hydrate (7.65 g, 50 mmol) in 100 ml tetrahydrofuran at 0° was added dropwise a solution of diisopropylethylamine (8.7 ml, 50 mmol) in 50 ml tetrahydrofuran. This was followed by addition of dicyclohexylcarbodiimide (10.315 g, 50 mmol). The reaction was stirred at 0° for 2 hours and then left for overnight stirring at room temperature. The precipitated urea was filtered off, solvents stripped down and the residue diluted with ethyl acetate (200 ml). The organic solution was washed sequentially with saturated aqueous sodium hydrogen carbonate (2×100 ml), saturated aqueous sodium chloride (2×100 ml), dried over sodium sulfate, filtered and concentrated to give crude product which on crystallization from ethyl ether gave 7.05 g pure product. Concentration of the mother liquor solution afforded 4.57 g crystalline product. An additional 1.35 g product was obtained by chromatographic purification of the crude product obtained from the left over mother liquors (40 g silica gel, 4:1 hexane/ethyl acetate). Thus, a total of 12.96 g of the title D compound was obtained. m.p.=104°–105°, $[\alpha]_D = -17.5°$ (c=1.2, MeOH).

Elemental analysis calc'd for $C_{24}H_{32}N_2O_5$: C, 64.30; H, 8.15; N, 7.14; Found: C, 64.12; H, 8.16; N, 7.02.

E. t-Butyloxycarbonylphenylalanyl leucine

Sodium hydroxide (1N; 12 ml, 12 mmol) was added to a 40 ml methanol solution of (S)-<α-[[(1,1-dimethylethoxy)carbonyl]amino]cyclohexanepropanoic acid, methyl ester (3.92 g, 10 mmol) and a chromatography check after one hour revealed total disappearance of starting material. The solvents were removed on rotary evaporator. The resulting white solid was suspended in 10 ml of water and 50 ml of ethyl acetate, acidified to pH=3.5 using 1N hydrochloric acid and the two layers separated. The aqueous layer was reextracted with ethyl acetate (3×30 ml), combined organic extracts dried over sodium sulfate and concentrated to give 3.54 g of the title E compound.

F. [(1,1-Dimethylethoxy)carbonyl]-L-phenylalanyl]-N-[(1S)-1-(cyclohexylmethyl)-2-hydroxy-2-(2-propyl-1,3-dithian-2-yl)ethyl]-L-leucinamide The title E compound (415.8 mg, 1.1 mmol) and the title C compound (388.9 mg, 1.1 mmol) were dissolved in 5 ml dimethylformamide and cooled to 0°. N,N-diisopropylethylamine (191.4 μl, 1.1 mmol) was added and after 5 minutes, this was followed by sequential addition of 1-hydroxy benzoatriazole hydrate (168.3 mg, 1.1 mmol) and dicyclohexylcarbodiimide (227 mg, 1.1 mmol). The reaction was left for gradual warming and overnight stirring. Next day, the reaction mixture was diluted with ethyl acetate (35 ml), the urea filtered off and the filtrate washed sequentially with water (2×20 ml), saturated sodium hydrogen carbonate (2×20 ml), 10 percent citric acid (1×20 ml), and saturated sodium chloride (1×20 ml). Drying with anhydrous sodium sulfate and concentration afforded 821 mg of crude product which upon chromatographic purification yielded 621 mg of the title F compound, m.p.=87°–92°, $[\alpha]_D = -35.0°$ (c=0.34, MeOH).

Elemental analysis calc'd for $C_{36}H_{59}N_3O_5S_2 \cdot 0.6H_2O$: C, 62.77; H, 8.81; N, 6.10; S, 9.31; Found: C, 62.84; H, 8.60; N, 6.00; S, 9.13.

G. [(1,1-Dimethylethoxy)carbonyl]-L-phenylalanyl-N-[(1S)-1-(cyclohexylmethyl)-2-hydroxy-3-oxohexyl]-L-leucinamide The title F compound (338.5 mg, 0.5 mmol) was dissolved in 12 ml acetonitrile and diluted with 3 ml water. Ammonium ceric nitrate (1.096 g, 2.0 mmol) was added to this solution and after 20 minutes, the reaction mixture was diluted with water (40 ml) and extracted with ether (3×30 ml). The combined organic extracts were dried over anhydrous sodium sulfate and concentrated to give 378 mg of residue which upon chromatographic purification yielded 140 mg of the title G compound, m.p.=149°–152°.

Elemental analysis calc'd for $C_{33}H_{53}N_3O_6$: C, 67.43; H, 9.09; N, 7.15; Found: C, 67.14; H, 9.40; N, 7.03.

H. (S)-[(1,1-Dimethylethoxy)carbonyl]-L-phenylalanyl-N-[1-(cyclohexylmethyl)-2,3-dioxohexyl]-L-leucinamide A solution of the title G compound (58.7 mg, 0.1 mmol) in 3 ml methylene chloride was added to a suspension of Dess Martin periodinane (65 mg, 0.15 mmol) and t-butylalcohol (12 mg, 0.15 mmol) in 2 ml methylene chloride. The reaction mixture was vigorously stirred. A TLC check after 6 hours revealed incomplete reaction; hence excess Dess Martin reagent (153 mg, 0.45 mmol) and t-butylalcohol (35 mg, 0.45 mmol) was added along with 5 ml methylene chloride and the reaction mixture left for overnight stirring. Next day, the reaction was judged complete by TLC. The reaction mixture was filtered through celite, the filtrate concentrated and the residue chromatographed to give 51 mg of the title compound. m.p.=134°–143°, $[\alpha]_D = -36.6°$ (c=0.61, MeOH).

Elemental analysis calc'd for $C_{33}H_{51}N_3O_6$: C, 67.66; H, 8.78; N, 7.17; Found: C, 67.52; H, 8.71; N, 7.13.

EXAMPLE 2

(S)-(Cyclopentylcarbonyl)-L-phenylalanyl-N-[1-(cyclohexylmethyl)-2,3-dioxohexyl]-L-leucinamide A. N-(L-Phenylalanyl)-L-leucine, methyl ester, monohydrochloride The compound from part D of Example 1 (12.01 g, 31 mmol) was dissolved in hydrochloric acid/acetic acid solution (62 mL), reacted for one hour and concentrated to give an oily residue. It was triturated with toluene (3×60 mL), and concentrated yielding 10 g of the title A compound.

B. N-[N-(Cyclopentylcarbonyl)-L-phenylalanyl]-L-leucine, methyl ester

Cyclopentane carboxylic acid (1.65 mL, 15.2 mmol) was added to a solution of the title A compound (5.0 g, 15.2 mmol) in dimethylformamide (60 mL) and cooled to 0° C. 1-Hydroxybenzotriazole (2.33 g, 15.2 mmol), N,N-diisopropylethylamine (2.93 mL, 17 mmol) and dicyclohexylcarbodiimide (3.14 g, 15.2 mmol) were added sequentially. After 16 hours at 0° C., the reaction mixture was filtered and concentrated. The residue was taken in ethyl acetate (250 mL), washed with water (3×150 mL), saturated sodium bicarbonate (150 mL), saturated sodium chloride (150 mL), dried and concentrated, yielding 6.0 g of crude product. Purification by flash chromatography afforded 3.40 g of the title B compound. m.p.=170°–171° C., $[\alpha]_D = -23.9°$ (c=1.18, MeOH).

Elemental analysis calc'd for $C_{22}H_{32}N_2O_4 \cdot 0.13H_2O$: C, 67.60; H, 8.32; N, 7.17; Found: C, 67.57; H, 8.31; N, 7.20.

C. N-[N-(Cyclopentylcarbonyl)-L-phenylalanyl]-L-leucine

Sodium hydroxide (1N; 12.36 mL, 12 mmol) was added to a solution of the compound of part B (2.04 g, 5.3 mmol) in methanol (20 mL). After five hours, the reaction mixture was concentrated and the residue was taken up in a mixture of water (20 mL) and ethyl acetate (50 mL) and acidified to pH 1.8. The layers were separated and aqueous layer was reextracted with ethyl acetate (3×75 mL). The combined organic extracts were dried and concentrated yielding 1.84 g of product, m.p. 148°-151° C. $[\alpha]_D = -12.9°$ (c=1.19, MeOH).

Elemental analysis calc'd for $C_{21}H_{30}N_2O_4 \cdot 1.34H_2O$: C, 63.28; H, 8.26; N, 7.03; Found: C, 63.32; H, 7.77; N, 7.01.

D. (Cyclopentylcarbonyl)-L-phenylalanyl-N-[(1S)-1-(cyclohexylmethyl)-2-hydroxy-2-(2-propyl-1,3-dithian-2-yl)ethyl]-L-leucinamide The compound of part C in Example 1 (707 mg, 2 mmol) was added to a solution of the title C compound from this Example (748 mg, 2 mmol) in tetrahydrofuran (8 mL) and cooled to 0° C. 1-Hydroxybenzotriazole (306 mg, 2 mmol), N,N-diisopropylethylamine (383 µl, 2.2 mmol), and dicyclohexylcarbodiimide (413 mg, 2 mmol) were added sequentially. After 16 hours at 0° C., the reaction mixture was filtered and concentrated. The reaction was taken up in ethyl acetate (50 mL), washed with water (2×30 mL), saturated sodium bicarbonate (2×40 mL), 10 percent citric acid (40 mL), saturated sodium chloride (40 mL), dried and concentrated. Purification of the crude product (1.2 g) by flash chromatography yielded 936 mg of pure product.

Elemental analysis calc'd for $C_{37}H_{60}N_3O_4S_2$: C, 65.83; H, 8.96; N, 6.23; Found: C, 65.62; H, 8.78; N, 6.19.

E. (Cyclopentylcarbonyl)-L-phenylalanyl-N-[(1S)-1-(cyclohexylmethyl)-2-hydroxy-3-oxohexyl]-L-leucinamide, isomer A A 20 ml methanol solution of thallic nitrate trihydrate (1.05 g, 1.18 mmol) was added to a solution of the title D compound (799 mg, 1.18 mmol) in methanol (40 mL) and ethyl acetate (20 mL). After 10 minutes the reaction mixture was filtered, concentrated and residue was taken in ethyl acetate (150 mL) and water (100 mL). The layers were separated and aqueous layer was extracted with ethyl acetate (2×120 mL). The combined organic portions were washed with 10 percent citric acid (150 mL), dried and concentrated affording 2.5 g of crude compound. Purification by flash chromatography yielded 573 mg pure product, m.p. 169° C. $[\alpha]_D = -61.3°$ (c=1.19, $CH_3OH$).

Elemental analysis calc'd for $C_{34}H_{53}N_3O_5 \cdot 0.63H_2O$: C, 68.62; H, 9.19; N, 7.06; Found: C, 68.79; H, 8.92; N, 6.99.

F. (S)-(Cyclopentylcarbonyl)-L-phenylalanyl-N-[1-(cyclohexylmethyl)-2,3-dioxohexyl]-L-leucinamide A solution of the hydroxy ketone of part E (268 mg, 0.46 mmol) was added to a suspension of Dess Martin reagent (389 mg, 0.91 mmol) and t-butylalcohol (68 mg, 0.92 mmol) in methylene chloride (40 mL). After five hours, reaction mixture was filtered and concentrated yielding 666 mg of crude product which was subjected to chromatographic purification affording 217 mg of the title compound, m.p.=152°-161° C. $[\alpha]_D = -59.1°$ (c=0.45, $CHCl_3$).

Analysis calc'd for $C_{34}H_{51}N_3O_5 \cdot 1.03H_2O$: C, 70.19; H, 8.84; N, 7.22; Found: C, 70.12; H, 8.79; N, 7.12.

EXAMPLE 3

[(1,1-Dimethoxyethoxy)carbonyl]-N-[(1S)-1-(cyclohexylmethyl)-2,3-dioxohexyl]-L-histidinamide A. N-[(1,1-Dimethoxyethoxy)carbonyl]-1-[(4-methylphenyl)sulfonyl]-L-histidine N-[(1,1-Dimethoxyethoxy)carbonyl]-L-histidine (12.7 g, 50 mmol) was dissolved in a solution of sodium carbonate (10.6 g, 100 mmol) in 150 ml water and cooled to 10°. p-Toluenesulfonylchloride (12.8 g, 67 mmol) was added in very small portions over a period of 30 minutes while maintaining vigorous stirring and controlling the temperature between 10°-15°. After the addition was complete, the reaction mixture was warmed to room temperature and stirring continued for an additional 4 hours. The reaction mixture was extracted twice with ethyl ether (75 ml) and the organic portions were discarded. The aqueous layer was acidified with 1N hydrochloric acid, extracted twice with ethyl acetate (150 ml) and the combined organic extracts were dried and concentrated to give an oily residue. Crystallization from ethyl acetate afforded 9.42 grams of the title A compound. m.p.=120°, $[\alpha]_D = 15.3°$ (c=1.66, $CH_3OH$).

Analysis calc'd for $C_{18}H_{23}N_3O_6S \cdot 0.14H_2O$: C, 52.48; H, 5.69; N, 10.20; S, 7.78; Found: C, 52.72; H, 5.70; N, 9.72; S, 8.09.

B. [(1,1-Dimethoxyethoxy)carbonyl]-N-[(1S)-1-(cyclohexylmethyl)-2-hydroxy-2-(2-propyl-1,3-dithian-2-yl)ethyl]-1-[(4-methylphenyl)sulfonyl]-L-histidinamide, isomer A Triethylamine (108 µl, 0.775 mmol) was added dropwise to a solution of the title A compound (133 mg, 0.325 mmol) and α-[(S)-1-amino-2-cyclohexylethyl]-2-propyl-1,3-dithiane-2-methanol, isomer A, monohydrochloride (88.4 mg, 0.25 mmol) in 2.5 ml methylene chloride at 0°. After 5 minutes diphenylphosphoryl azide (70 µl, 0.325 mmol) was added, and the reaction mixture was stirred for 2 hours at 0° and then overnight at room temperature. Next day, the reaction mixture was concentratd on a rotary evaporator (to remove excess triethylamine), the residue diluted with 15 ml methylene chloride and 15 ml saturated sodium hydrogen carbonate and the two layers were separated. The aqueous layer was reextracted twich with methylene chloride and the combined organic extracts were dried over sodium sulfate and concentrated to give 292 mg residue. Chromatographic purification yielded 125 mg of the title B compound. m.p. 83°-88°; $[\alpha]_D = -16.5°$ (c=1.3, MeOH).

Analysis calc'd for $C_{34}H_{52}N_4S_3O_6$: C, 57.60; H, 7.39; N, 7.90; S, 13.57; Found: C, 57.71; H, 7.48; N, 7.64; S, 13.71.

C. [(1,1-Dimethoxyethoxy)carbonyl]-N-[(1S)-1-(cyclohexylmethyl)-2-hydroxy-3-oxohexyl]-1-[(4-methylphenyl)sulfonyl]-L-histidinamide, isomer A Thallic nitrate trihydrate (844 mg, 1.9 mmol) was added in one portion to a 40 ml 1:1 methanol/ethyl ether solution of the title B compound (674 mg, 0.95 mmol) at 0°. After 15 minutes, the reaction mixture was filtered through celite and the solids washed twice with ethyl acetate (25 ml). Concentration of the solid gave a residue which upon chromatographic purification yielded 399 mg of the title C compound. m.p. 67°-76°, $[\alpha]_D = -42.6°$ (c=1.21, MeOH).

Analysis calc'd for $C_{31}H_{46}N_4O_7S \cdot 2.2H_2O$: C, 58.85; H, 7.57; N, 8.86; Found: C, 59.09; H, 7.47; N, 8.56.

D. [(1,1-Dimethoxyethoxy)carbonyl]-N-[(1S)-1-(cyclohexylmethyl)-2,3-dioxohexyl]-1-[(4-methylphenyl)sulfonyl]-L-histidinamide Dess martin periodinane (308.5 mg, 0.73 mmol) was added to a solution of the title C compound (300 mg, 0.485 mmol) and t-butanol (53 mg, 0.73 mmol) in 5 ml dichloromethane. After 2 hours at room temperature, the reaction mixture was diluted with 20 ml dichloromethane and washed with an aqueous solution of sodium bicarbonate and sodium sulfite. Drying and concentration afforded a residue which upon flash chromatographic purification provided 288 mg of the title D compound, m.p. 60°–67°.

E. [(1,1-Dimethoxyethoxy)carbonyl]-N-[(1S)-1-(cyclohexylmethyl)-2,3-dioxohexyl]-L-histidinamide 1-Hydroxybenzotriazole (12.2 mg, 0.08 mmol) was added in one portion to a solution of the title D compound (12.2 mg, 0.02 mmol) in 2 ml methanol. After 2 hours at room temperature, solvents were removed on rotary evaporator and the residue purified by flash chromatography to provide 10 mg of the title compound.

EXAMPLES 4 TO 25

Following the procedures of Example 1 and outlined above, the following additional compounds of formula I within the scope of the present invention can be prepared.

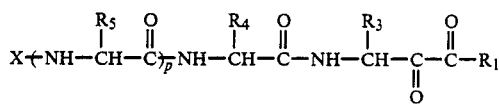

| Ex. No. | $R_1$ | $R_3$ | $R_4$ | $R_5$ | X |
|---|---|---|---|---|---|
| 4 | —CH₂—CH₂—CH₃ | —CH₂—cyclohexyl | —CH₂—(4-imidazolyl) | —CH₂—phenyl | (CH₃)₃C—O—C(O)— |
| 5 | —CH₂—CH(CH₃)₂ | —CH₂—cyclohexyl | —CH₂—(4-imidazolyl) | —CH₂—phenyl | H₃C—O—C(O)— |
| 6 | —CH₂—CH₂—CH₃ | —CH₂—cyclohexyl | —CH₂—(4-imidazolyl) | —CH₂—phenyl | cyclopentyl-C(O)— |
| 7 | —CH₂—CH₂—CH₃ | —CH₂—cyclohexyl | —CH₂—(4-imidazolyl) | —CH₂—phenyl | pyrrolidinyl-N—C(O)— |
| 8 | —CH₂—CH₂—CH₃ | —CH₂—cyclohexyl | —CH₂—(4-imidazolyl) | —CH₂—phenyl | morpholinyl-N—C(O)— |
| 9 | —CH₂—CH₂—CH₃ | —CH₂—cyclohexyl | —CH₂—(4-imidazolyl) | —CH₂—phenyl | —CH₃—N(piperazinyl)N—C(O)— |
| 10 | —CH₂—CH₂—CH₃ | —CH₂—cyclohexyl | —CH₂—CH(CH₃)₂ | —CH₂—phenyl | —CH₃—N(piperazinyl)N—C(O)— |
| 11 | —CH₂—CH₂—CH₃ | —CH₂—cyclohexyl | —CH₂—CH(CH₃)₂ | —CH₂—phenyl | morpholinyl-N—C(O)— |

-continued

| Ex. No. | R₁ | R₃ | R₄ | R₅ | X |
|---|---|---|---|---|---|
| 12 | −CH₂−(phenyl) | −CH₂−(cyclohexyl) | −CH₂−(imidazol-4-yl, NH) | −CH₂−(phenyl) | morpholino-C(=O)− |
| 13 | −(phenyl) | −CH₂−(cyclohexyl) | −CH₂−(imidazol-4-yl, NH) | −CH₂−(phenyl) | morpholino-C(=O)− |
| 14 | −CH(CH₃)₂ | −CH₂−(cyclohexyl) | −CH₂−CH(CH₃)₂ | −CH₂−(phenyl) | H₃C−N(piperazine)N−C(=O)− |
| 15 | −CH₂−(imidazol-4-yl, HN) | −CH₂−(cyclohexyl) | −CH₂−CH(CH₃)₂ | −CH₂−(phenyl) | (pyrrolidinyl)N−C(=O)− |
| 16 | −CH₂−(pyridin-2-yl) | −CH₂−(cyclohexyl) | −CH₂−CH(CH₃)₂ | −CH₂−(phenyl) | morpholino-C(=O)− |
| 17 | −CH₂−CH₂−(phenyl) | −CH₂−CH(CH₃)₂ | −CH₂−(imidazol-4-yl, NH) | −CH₂−(phenyl) | H₃C−CH₂−O−C(=O)− |
| 18 | −CH₂−(phenyl) | −CH₂−(cyclohexyl) | −CH₂−(imidazol-4-yl, NH) | −CH₂−(phenyl) | H₃C−C(=O)− |
| 19 | −CH₂−CH₂−CH₃ | −CH₂−(cyclohexyl) | −CH₂−CH(CH₃)₂ | −CH₂−(naphthyl) | morpholino-C(=O)− |
| 20 | −CH₂−CH₂−CH₃ | −CH₂−(cyclohexyl) | −CH₂−CH(CH₃)₂ | −CH₂−CH₂−(phenyl) | morpholino-C(=O)− |
| 21 | −CH₂−CH₂−CH₃ | −CH₂−(cyclohexyl) | −(CH₂)₄−NH₂ | −CH₂−(phenyl) | morpholino-C(=O)− |

-continued

| Ex. No. | R₁ | R₃ | R₄ | R₅ | X |
|---|---|---|---|---|---|
| 22 | —CH₂—CH₂—CH₃ | —CH₂—(cyclohexyl) | —CH₂—CO₂H | —CH₂—(1-naphthyl) | morpholine-N—C(=O)— |
| 23 | —CH₂—CH₂—CH₃ | —CH₂—(cyclohexyl) | —CH₂—CH₂—CO₂H | —CH₂—(1-naphthyl) | morpholine-N—C(=O)— |
| 24 | —CH₂—CH₂—CH₃ | —CH₂—(cyclohexyl) | —CH₂—(4-hydroxyphenyl) | —CH₂—(1-naphthyl) | morpholine-N—C(=O)— |
| 25 | —CH₂—CH₂—CH₃ | —CH₂—(cyclohexyl) | —CH₂—C(=O)—NH₂ | —CH₂—(1-naphthyl) | morpholine-N—C(=O)— |

What is claimed is:

1. A compound having the formula $$X-(NH-\underset{R_5}{CH}-\underset{}{C(=O)})_p-NH-\underset{R_4}{CH}-C(=O)-NH-\underset{R_3}{CH}-\underset{O}{\overset{}{C(=O)}}-C(=O)-R_1$$

wherein
X is $R_6-(CH_2)_m-$,

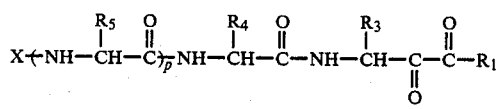

$$R_6-(CH_2)_m-\overset{O}{\overset{\|}{C}}-(NH-\underset{R_{10}}{CH}-\overset{O}{\overset{\|}{C}})_q-,\ R_6-(CH_2)_m-O-\overset{O}{\overset{\|}{C}}-,$$

$$R_6-O-(CH_2)_n-\overset{O}{\overset{\|}{C}}-,\ R_6-(CH_2)_m-NH-\overset{O}{\overset{\|}{C}}-,$$

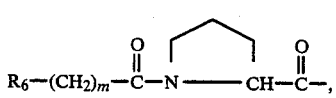, $R_6(CH_2)_m-SO_2-$ or $$R_6-(CH_2)_m-\underset{\underset{R_6'}{(CH_2)_{m'}}}{CH}-\overset{O}{\overset{\|}{C}}-,$$

R₁ is hydrogen, alkyl, arylalkyl, aryl, heteroalkyl or a fully saturated, partially saturated, or unsaturated monocyclic heterocyclic ring of 5 or 6 atoms which is attached to $$-\underset{O}{\overset{}{C}}-$$

by way of an available carbon atom;

representss a heterocyclic ring of the formula

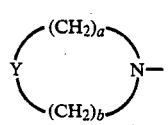

wherein
Y is —CH$_2$, O, S, or N—R$_9$, a is an integer from 1 to 4, and b is an integer from 1 to 4 provided that the sum of a plus b is an integer from 2 to 5;

R$_3$, R$_4$, R$_5$ and R$_{10}$ are independently selected from hydrogen, lower alkyl, halo substituted lower alkyl, —(CH$_2$)$_n$-aryl, —(CH$_2$)$_n$-heterocyclo, —(CH$_2$)$_n$—OH, —(CH$_2$)$_n$—O-lower alkyl, —(CH$_2$)$_n$—NH$_2$, —(CH$_2$)$_n$—SH, —(CH$_2$)$_n$—S-lower alkyl, —(CH$_2$)$_n$—O—(CH$_2$)$_g$—OH, —(CH$_2$)$_n$—O—(CH$_2$)$_g$—NH$_2$, —(CH$_2$)$_n$—S—(CH$_2$)$_g$—OH, —(CH$_2$)$_n$—C(=O)—OH, —(CH$_2$)$_n$—S—(CH$_2$)$_g$—NH$_2$,

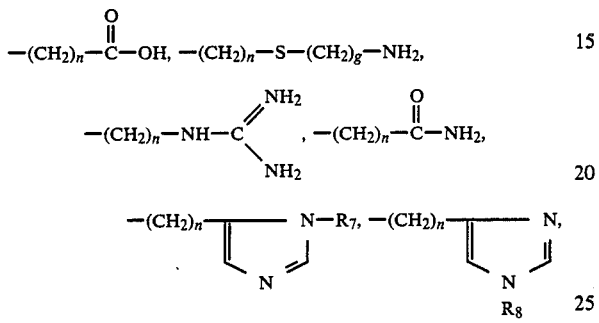

and —(CH$_2$)$_n$-cycloalkyl;

R$_6$ and R$_6'$ are independently selected from lower alkyl, cycloalkyl, aryl and heterocyclo;

p is zero or one;

q is zero or one;

m and m' are independently selected from zero and an integer from 1 to 5;

n is an integer from 1 to 5;

g is an integer from 2 to 5;

R$_7$ is

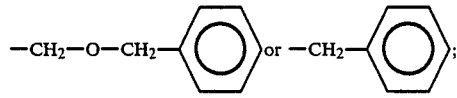

R$_8$ is 2,4-dinitrophenyl,

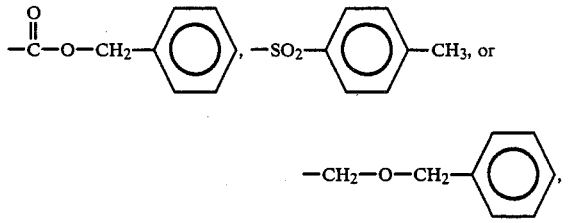

R$_9$ is hydrogen, lower alkyl,

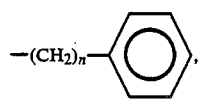

or —(CH$_2$)$_n$-cycloalkyl;

wherein the term heterocyclo refers to fully saturated or unsaturated rings of 5 or 6 atoms containing one or two oxygen or sulfur atoms and/or one to four nitrogen atoms provided that the total number of hetero atoms is 4 or less, and wherein the ring is attached by way of an available carbon atom, and further including bicyclic rings wherein the hetero-containing 5- or 6-membered ring is fused to a benzene ring.

2. A compound in accordance with claim 1 wherein X is

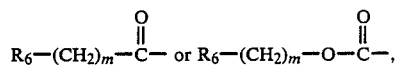

R$_6$ is selected from straight or branched chain lower alkyl of up to 5 carbons, cycloalkyl of 4 to 6 carbons, phenyl, 1-naphthyl, and 2-naphthyl;

m is selected from zero, one and two;

R$_1$ is alkyl, arylalkyl, aryl, or heteroalkyl;

R$_3$ is straight or branched chain lower alkyl of 3 to 5 carbons, —(CH$_2$)$_n$-cyclopentyl, —(CH$_2$)$_n$-cyclohexyl, or

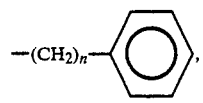

wherein n is an integer from 1 to 3;

R$_4$ is hydrogen, straight or branched chain lower alkyl of up to 5 carbons, —(CH$_2$)$_4$—NH$_2$,

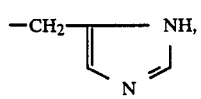

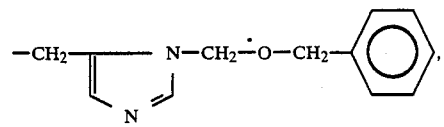

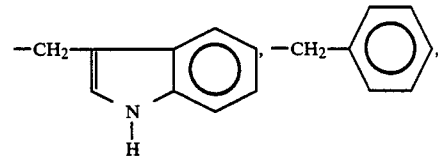

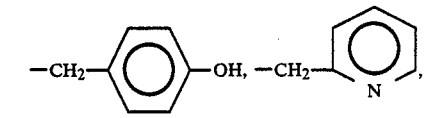

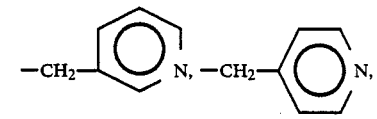

-continued
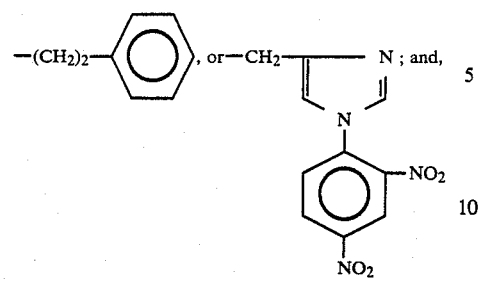
R₅ is straight or branched chain lower alkyl of up to 5 carbons,
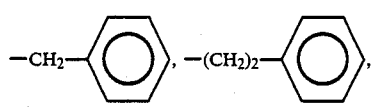
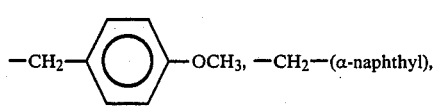
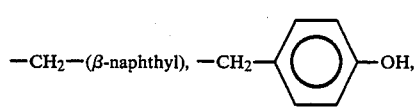
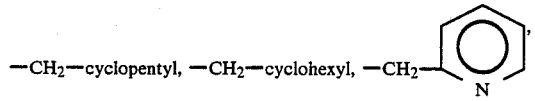
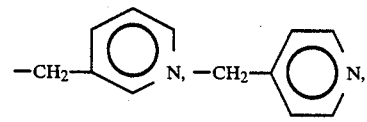
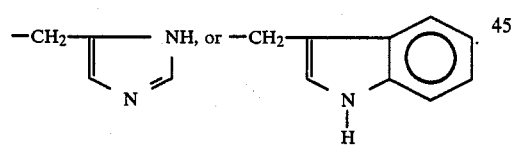
3. A compound in accordance with claim 1 wherein X is
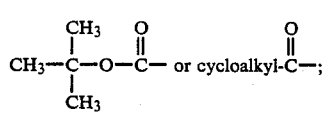
R₁ is —CH₂—CH₂—CH₃,
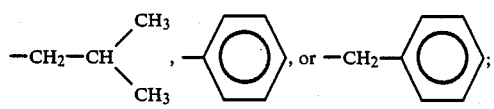
R₃ is
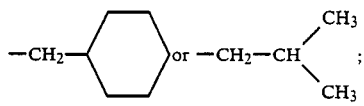
R₄ is
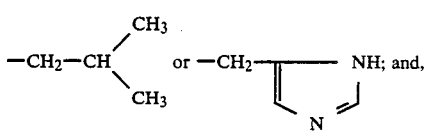
R₅ is
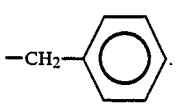
4. A compound in accordance with claim 1 wherein X is
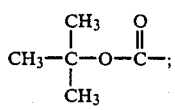
R₁ is
—(CH₂)₂CH₃;
R₃ is
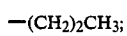
R₄ is
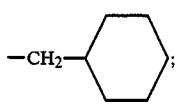; and,
R₅ is
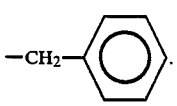
5. A compound in accordance with claim 1 wherein X is
R₁ is —(CH₂)₂CH₃;
R₃ is

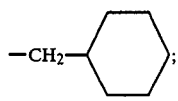

R4 is

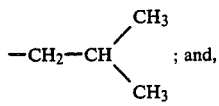; and,

R5 is

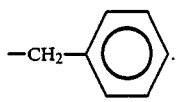.

6. A compound in accordance with claim 1 wherein X is

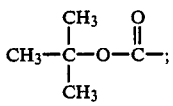

R1 is $(CH_2)_2CH_3$;
R3 is

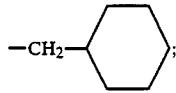;

R4 is

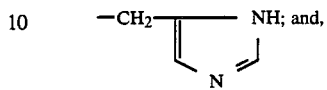; and, p is zero.

7. A compound in accordance with claim 1 having the name (S)-[(1,1-dimethylethoxy)carbonyl]-L-phenylalanyl-N-[1-(cyclohexylmethyl)-2,3-dioxohexyl]-L-leucinamide.

8. A compound in accordance with claim 1 having the name (S)-(cyclopentylcarbonyl)-L-phenylalanyl-N-[1-(cyclohexylmethyl)-2,3-dioxohexyl]-L-leucinamide.

9. A compound in accordance with claim 1 having the name [(1,1-dimethoxyethoxy)carbonyl]-N-[(1S)-1-(cyclohexylmethyl)-2,3-dioxohexyl]-L-histidinamide.

10. A pharmaceutical composition for the inhibition of renin comprising a pharmaceutically acceptable carrier and a compound of claim 1.

11. A method of inhibiting renin in a mammalian species comprising administering a pharmaceutical composition of claim 10 to a mammalian species in need thereof.

* * * * *